United States Patent
Sato (12)

(10) Patent No.: US 6,328,568 B1
(45) Date of Patent: Dec. 11, 2001

(54) METHOD FOR MANUFACTURING METALLIC DENTAL CROWN AND MOLD MATERIAL FOR FORMING DENTAL CROWN OCCLUSAL PORTION USED FOR THE METHOD

(75) Inventor: Hiroshi Sato, Kanagawa-ken (JP)

(73) Assignee: Dental Supply Co., Kanagawa-ken (JP)

( * ) Notice: Subject to any disclaimer, the term of this patent is extended or adjusted under 35 U.S.C. 154(b) by 0 days.

(21) Appl. No.: 09/644,551

(22) Filed: Aug. 24, 2000

(30) Foreign Application Priority Data

Aug. 27, 1999 (JP) .................................................. 11-241291

(51) Int. Cl.[7] ..................................................... A61C 5/10
(52) U.S. Cl. ............................................. 433/223; 433/218
(58) Field of Search ...................................... 433/218, 219, 433/223

(56) References Cited

U.S. PATENT DOCUMENTS 5,073,113 * 12/1991 Hornig ................................. 433/223
5,613,854 * 3/1997 Sweatt .................................. 433/223
5,730,600 * 3/1998 Shoher et al. ....................... 433/223
5,775,913 * 7/1998 Updyke et al. ..................... 433/223
5,827,063 * 10/1998 Greenstein ..................... 433/223 X

* cited by examiner

Primary Examiner—Nicholas D. Lucchesi
(74) Attorney, Agent, or Firm—Wenderoth, Lind & Ponack, L.L.P.

(57) ABSTRACT

A method for manufacturing a metallic dental crown comprising making a model base out of a base formed on a tooth root in an oral cavity; capping only a top portion of the model base with a mold material for forming a dental crown occlusal portion which is made of plastic film and which has a shallow royal crown configuration; coating that area of an outer peripheral surface of the model base, which is not capped with the mold material for forming the dental crown occlusal portion, with wax to form a composite mold material for forming the dental crown integral with the mold material for forming the dental crown occlusal portion; and substitution molding the composite mold material for forming the dental crown with a metal material. A mold material for forming a dental crown occlusal portion used for manufacturing a metallic dental crown is also disclosed.

8 Claims, 3 Drawing Sheets

US 6,328,568 B1

METHOD FOR MANUFACTURING METALLIC DENTAL CROWN AND MOLD MATERIAL FOR FORMING DENTAL CROWN OCCLUSAL PORTION USED FOR THE METHOD

BACKGROUND OF THE INVENTION

1. Field of the Invention

This invention relates to a method for manufacturing a metallic dental crown to be capped on a base formed on a tooth root in an oral cavity and a mold material for forming a dental crown occlusal portion used for the method.

2. Related Art

As one treatment of a carious tooth in an oral cavity, it has heretofore been known that a model base is made out of a base formed on a treated tooth root, then a metallic dental crown is made out of such obtained model base and then, the metallic dental crown is capped on the base using an adhesive agent. This metallic dental crown is made by a method using a wax mold shown in FIGS. 1(A) to 1(F).

In FIGS. 1(A) and 1(B), reference numeral 1 denotes a model base templated from a base formed on a tooth root in an oral cavity. First, as shown in FIG. 1(A), an entire peripheral surface including a top face and an outer peripheral surface, of the model base 1 is coated with wax to form a wax-coated layer 2a having a predetermined thickness.

Then, as shown in FIG. 1(B), an occlusal portion 3 having precision concavities and convexities are formed on the top face of the wax-coated layer 2a by cutting and an external configuration thereof is properly shaped. Then, a lower end portion (a marginal portion 4 contacting the gum) of the wax-coated layer 2a is cut to obtain a wax mold material 2b.

Then, as shown in FIG. 1(C), the wax mold material 2b is removed from the model base 1 and a spool 5 is attached to the wax mold material 2b.

Then, as shown in FIG. 1(D), the wax mold material 2b attached with the spool 5 is placed in a casting mold and molten metal 9 of gold, silver or the like is poured therein through the spool 5 to burn the wax mold material 2b so as to be substituted with the molten metal.

Hence, the metallic dental crown 7 as shown in FIG. 1(E) is accomplished. The metallic dental crown 7 thus obtained is, as shown in FIG. 1(F), capped on the base 8 in the oral cavity and firmly attached thereto by an adhesive agent.

However, the conventional dental crown manufacturing method has such problems that trained techniques and much time are required for the work for shaping the wax mold material 2b into a tooth shape, especially the work for cutting the precision occlusal shape 3 and as a consequence, the manufacturing cost for the metallic dental crown 7 is increased. In addition, uneven quality of the metallic dental crowns 7 is resulted.

SUMMARY OF THE INVENTION

It is, therefore, an object of the present invention to provide a novel method for manufacturing a metallic dental crown and a mold material for forming a dental crown occlusal portion used in the method, in which the above-mentioned problems inherent in the related art can be solved fundamentally.

To achieve the above object, from one aspect of the present invention, there is essentially provided a method for manufacturing a metallic dental crown comprising making a model base out of a base formed on a tooth root in an oral cavity; capping only a top portion of the model base with a mold material for forming a dental crown occlusal portion which is made of plastic film and which has a shallow royal crown configuration; coating that area of an outer peripheral surface of the model base, which is not capped with the mold material for forming the dental crown occlusal portion, with wax to form a composite mold material for forming the dental crown integral with the mold material for forming the dental crown occlusal portion; and substitution molding the composite mold material for forming the dental crown with a metal material.

From another aspect of the invention, there is also provided a mold material for forming a dental crown occlusal portion used for manufacturing a metallic dental crown, comprising a cover portion having an occlusal portion for covering a top face of a model base templated from a base formed on a tooth root in an oral cavity, an engagement portion standing down from a peripheral edge portion of the cover portion and engageable with a peripheral surface of a top portion of the model base, the cover portion and the engagement portion being formed from an integrally formed plastic film, the mold material for forming a dental crown occlusal portion exhibiting, as a whole, a shallow crown configuration.

It is preferred that a lower end face of the engagement portion has a shear plane generally orthogonal to a peripheral surface thereof.

By virtue of the construction of the present invention, the above-mentioned object of the present invention can be solved fundamentally.

BRIEF DESCRIPTION OF THE DRAWINGS

For a full understanding of the true scope of the invention, the following detailed description should be read in conjunction with the drawings, wherein.

DETAILED DESCRIPTION OF THE INVENTION

One embodiment of the present invention will now be described with reference to FIGS. 2 and 3.

Figure 1A:
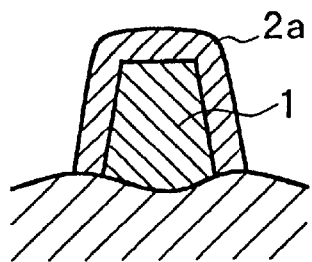
FIGS. 1(A) TO 1(F) are sectional views for sequentially explaining a conventional method for manufacturing a metallic dental crown.
Figure 1B:
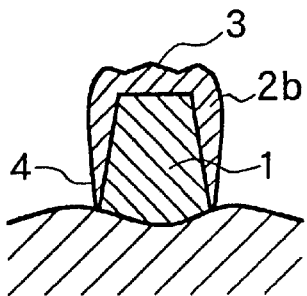
Figure 1C:
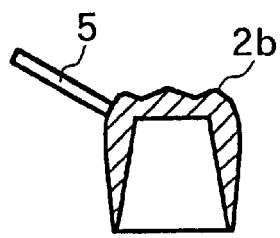
Figure 1D:
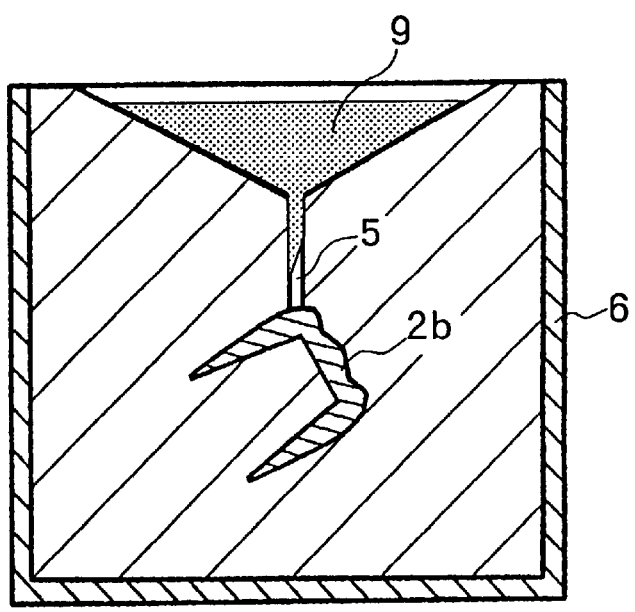
Figure 1E:
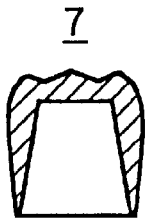
Figure 1F:
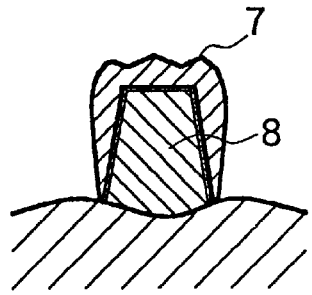
Figure 2A:
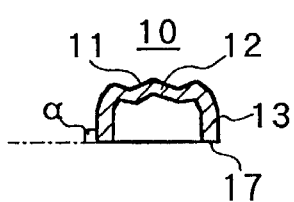
FIGS. 2(A) to 2(H) are sectional views for sequentially explaining a method for manufacturing a metallic dental crown according to the present invention.

FIG. 2(A), reference 10 denotes a mold material for forming a dental crown occlusal portion composed of a plastic film. The dental crown occlusal portion forming mold material 10 includes a cover portion 12 having an occlusal configuration 11 for covering a top face of a model base 1 templated from a base formed on a tooth root in an oral cavity and an engagement portion 13 projecting down from a peripheral edge portion of the cover portion 12 and engageable with a top portion peripheral surface of the model base 1. The cover portion 12 and the engagement portion 13 being formed from an integrally formed plastic film. The mold material 10 exhibits a shallow royal crown configuration as a whole.

An angle α formed by a lower end face 17 of the engagement portion 13 with respect to a peripheral surface thereof is set to approximately right angles. The lower end face 17 is a shear plane obtained by cutting with a cutting tool.

Figure 3A:
FIGS. 3(A) to 3(E) are sectional views for sequentially explaining a method for manufacturing a mold material for forming a dental crown occlusal portion used in the method for manufacturing a metallic dental crown.
Figure 3B:
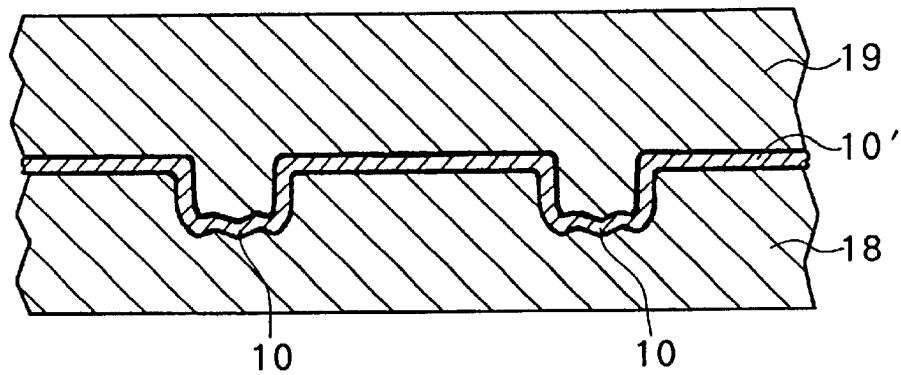

The dental crown occlusal portion forming mold material 10 can be continuously mass-produced by subjecting a thermoplastic film 10' shown in FIG. 3(A) to hot press working using a female mold 18 and a male mold 19 shown in FIG. 3(B).

Figure 3C:
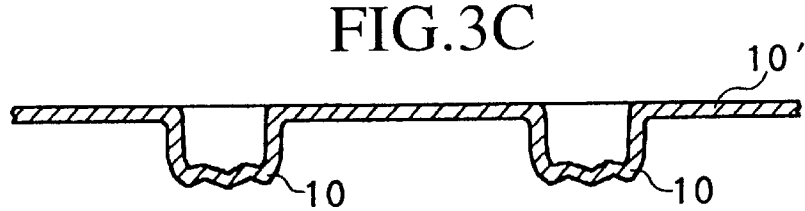

As shown in FIG. 3(C), the removed press formed article includes a plurality of dental crown occlusal portion forming mold materials 10 press formed on a sheet of film 10'.

Figure 3D:
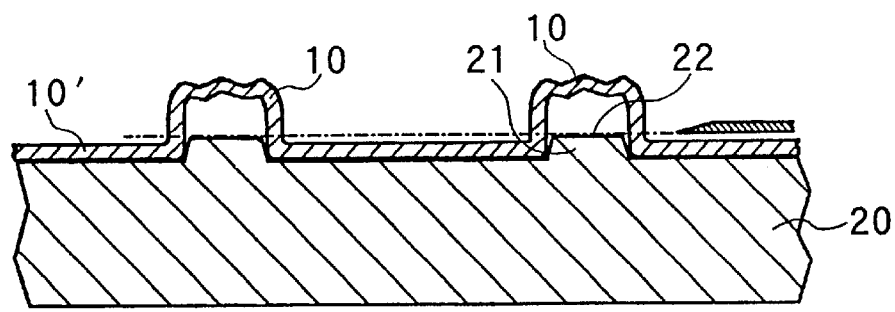

The press formed film 10' is, as shown in FIG. 3(D), laid on a surface of a scale table 20. Positioning projections 21 formed on the surface of the scale table 20 are brought into engagement with openings formed in basal portions of the dental crown occlusal portion forming mold materials 10. That is, the projections 21 are lightly engaged for positioning with the basal portion openings of the dental crown occlusal portion forming mold materials 10.

Then, as shown in FIG. 3(D), a cutting tool is moved horizontally along a flat top face 22 of each positioning projection 21 from sideways of the engagement portion 13 of the dental crown occlusal portion forming mold material 10 to cut a basal portion of the engagement portion 13. By doing so, the lower end face 17 of the engagement portion 13 becomes generally orthogonal to the peripheral surface thereof and exhibits a shear plane obtained by cutting with a cutting tool.

Figure 3E:
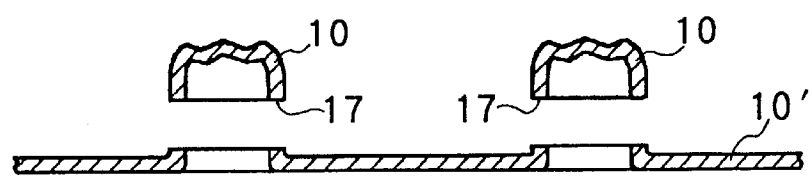

Preferably, as shown in FIG. 3(E), the height of the engagement portion 13 is arranged to be slightly higher than a preset height and the basal portion of the engagement portion 13 is cut at the preset height. That is, instead of cutting the basal portion of the engagement portion 13 at the same level as the surface of the film 10', the basal portion is cut at a location slightly away from the surface of the film 10'.

Preferably, the dental crown occlusal portion forming mold material 10, which includes the cover portion 12 and the engagement portion 13, is formed from an integrally formed plastic film which is abundant in flexibility.

As a suitable material of the mold material 10, ethylene-methyl-methacrylate is used. Or otherwise, a mixed material of ethylene-methyl-methacrylate and polyethylene is used. Any of them can give a favorable flexibility to the mold material 10. This material does not produce any harmful gas.

Figure 2B:
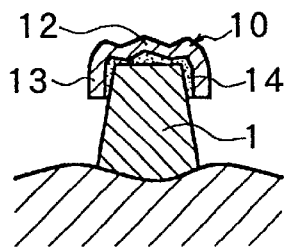

The dental crown occlusal portion forming mold material 10 is prepared. On the other hand, as shown in FIG. 2(B), the model base 1 is made out of the base 8 formed on the tooth root in the oral cavity and only the top portion of the model base 1 is capped with the dental crown occlusal portion forming mold material 10 which is made of plastic film and which exhibits a shallow royal crown configuration.

The dental crown occlusal portion forming mold material 10 and the model base 1 are peelably bonded to the top portion of the base 1 through an adhesive agent layer 14 such as the deformable soft wax which is interposed between the inner peripheral surface of the material 10 and the outer peripheral surface of the top portion of the base 1 and capped thereon.

After the dental crown occlusal portion forming mold material 10 is capped on the top portion of the base 1, the top face or the side face of the material 10 is pressed to deform and shape the material 10 while deforming the adhesive agent layer 14, until the material 10 becomes coincident with the shape of the patient's tooth.

Figure 2C:
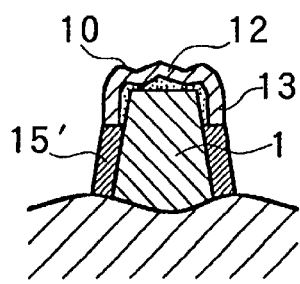
Figure 2D:
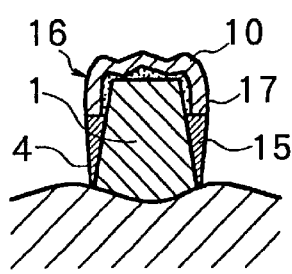

Then, as shown in FIG. 2(C), that area of the outer peripheral surface of the model base 1 which is not capped with the material 10 is coated with the wax 15', as shown in FIG. 2(D), the marginal portion 4, which can contact the gum, is cut and the wax mold portion 15 is formed. By doing so, a dental crown forming composite mold material 16 integral with the dental crown occlusal portion forming mold material 10 is formed.

The wax 15' forming the wax mold portion 15 is coated in such a manner as to be intimately contacted with the lower end face 17 (shear plane) of the engagement portion 13 of the dental crown occlusal portion forming mold material 10 composed of a plastic film and not to be expanded outward from the lower end face 17.

That is, it is such shaped that the wax mold portion 15 is intimately contacted with the end face 17 of the engagement portion 13 of the dental crown occlusal portion forming mold material 10 which is increased in bulk by the adhesive agent layer 14 composed of a soft wax while intimately contacting with that area of the outer peripheral surface of the model base 1 which is not capped with the material 10, so that the wax mold portion 15 is not expanded outward from the end face 17.

Figure 2E:
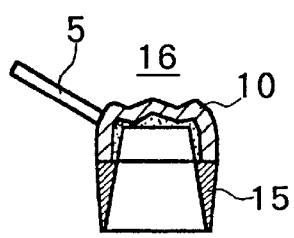

The resultant is, as shown in FIG. 2(E), removed from the model base 1. i.e., the dental crown forming composite mold material 16 composed of the dental crown occlusal portion forming mold material 10 and the wax mold portion 15 is removed from the model base 1 and the spool 5 is attached to the dental crown occlusal portion forming mold material 10.

Figure 2F:
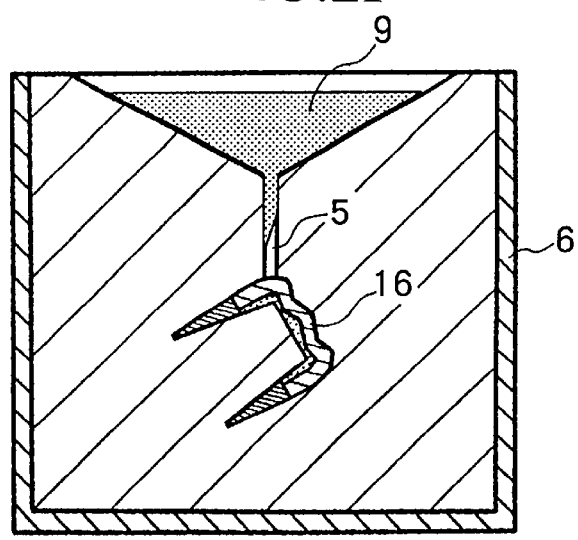

Then, as shown in FIG. 2(F), the dental crown forming composite mold material 16 attached with the spool 5 is placed in the casting mold 6 and the molten metal 9 such as gold and silver is poured therein through the spool 5 to burn the dental crown forming composite mold material 16 with the molten metal 9 so as to be substituted with the molten metal 9.

Figure 2G:
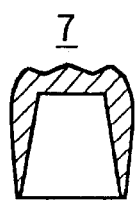
Figure 2H:
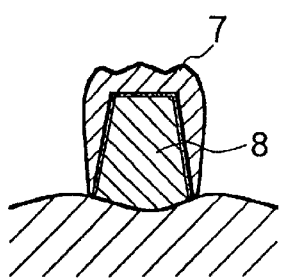

Thus, as shown in FIG. 2(G), the metallic dental crown 7 is accomplished. The metallic dental crown 7 thus obtained is capped on the base 8 in the oral cavity as shown in FIG. 2(H) and firmly attached thereto by an adhesive agent.

According to the present invention, the work for applying a configuration of the occlusal portion, which would otherwise be very troublesome, can be performed easily owing to a provision of the dental crown occlusal portion forming mold material, and the conventionally required work for shaping (cutting) the occlusal portion can be omitted. This makes it possible to extensively reduce the working time and to reduce the cost. Moreover, Metallic dental crowns having even quality can be manufactured without a need of high trained techniques which have conventionally been required.

Since the dental crown occlusal portion forming mold material is formed from an integrally formed plastic film, it can be manufactured on a mass production basis and very economically.

Moreover, by cutting the lower end face of the engagement portion of the dental crown occlusal portion forming mold material so as to have a shear plane which is approximately right angles with respect to the peripheral surface of the engagement portion, a sufficient joining strength can be obtained at the abutting surface between the wax and the dental crown occlusal portion forming mold material during the manufacture of the dental crown forming composite mold material. Also, the work for shaping the marginal portion can be performed easily.

Moreover, owing to a provision of the dental crown occlusal portion forming material composed of a plastic film which is abundant in flexibility, the material can easily be made coincident with the shape of the occlusal portion of the patient's tooth. And no harmful gas is produced.

Numerous modifications and alternative embodiments of the present invention will be apparent to those skilled in the art in view of the description described hereinbefore. Accordingly, this description is to be construed as illustrative only and is for the purpose of teaching those is skilled in the art the best mode of carrying out the invention. Details of the structure may be varied substantially without departing from the spirit of the invention and the exclusive use of all modifications which come within the scope of the appended claims is reserved.

What is claimed is:

1. A method for manufacturing a dental crown for use on a base framed on a tooth root in an oral cavity, said method comprising:

capping a top portion of said base with a flexible film, thereby forming a dental crown occlusal mold portion;

coating wax onto a peripheral surface of said base that is not capped with said flexible film, thereby forming a dental crown forming composite mold material; and substitution molding said dental crown forming composite mold material with a substitute material.

2. The method as claimed in claim 1, wherein said capping said top portion of said base with said flexible film further comprises peelably bonding said flexible film to said top portion of said base with an adhesive agent layer.

3. The method as claimed in claim 2, wherein said adhesive agent layer comprises deformable wax.

4. The method as claimed in claim 1, wherein said coating wax onto a peripheral surface of said base further comprises removing a portion of said wax from said base.

5. The method as claimed in claim 4, wherein said removing said portion of said wax further includes cutting said portion of said wax so as to annularly taper the cross-sectional shape of said wax that is not removed from said base.

6. The method as claimed in claim 1, wherein said substitute material comprises metal.

7. The method as claimed in claim 1, wherein said flexible film comprises plastic.

8. The method as claimed in claim 7, wherein said flexible film comprises ethylene-methyl-methacrylate or polyethylene.

* * * * *